United States Patent [19]

Haber

[11] 4,427,693

[45] Jan. 24, 1984

[54] ANTIINFLAMMATORY 4,5-DIARYL-α,α-BIS(POLYHALOMETHYL)-2-THIOPHENEMETHANAMINES

[75] Inventor: Stephen B. Haber, Wilmington, Del.

[73] Assignee: E. I. Du Pont de Nemours and Company, Wilmington, Del.

[21] Appl. No.: 316,661

[22] Filed: Nov. 2, 1981

Related U.S. Application Data

[63] Continuation-in-part of Ser. No. 288,994, Aug. 5, 1981, abandoned, which is a continuation-in-part of Ser. No. 220,772, Dec. 29, 1980, abandoned.

[51] Int. Cl.$^3$ .................... A61K 31/38; A61K 31/44; C07D 333/00; C07D 401/00

[52] U.S. Cl. .................... 424/275; 424/263; 549/74; 549/75; 546/256; 546/268

[58] Field of Search .................... 549/74, 75; 546/256, 546/268; 424/275, 263

[56] References Cited

U.S. PATENT DOCUMENTS

| | | | |
|---|---|---|---|
| 3,644,399 | 2/1972 | Brown et al. | 549/74 |
| 4,174,405 | 11/1979 | Relyea et al. | 549/74 |

*Primary Examiner*—Alan Siegel

[57] ABSTRACT

4,5-Diaryl-α,α-bis(polyhalomethyl)-2-thiophenemethanamines, such as 4,5-bis(4-fluorophenyl)-α,α-bis(trifluoromethyl)-2-thiophenemethanamine, useful for treating arthritis and/or alleviating pain.

33 Claims, No Drawings

ANTIINFLAMMATORY 4,5-DIARYL-α,α-BIS(POLYHALOMETHYL)-2-THIOPHENEMETHANAMINES

BACKGROUND OF THE INVENTION

This invention relates to antiinflammatory diaryl thiophenes.

A number of references, such as *Compt. Rend.*, 242, 1738 (1956) and *Z. CHem.*, 13, 57 (1973), disclose the preparation of 2,3-diarylthiophenes.

G. F. Il'in, et al. in *J. Org. Chem.* (USSR), 15, 2012 (1979) disclose the reaction of thiophene with N-methylsulfonylhexafluoroacetone imine to give N-methanesulfonyl-α,α-bis(trifluoromethyl)-2-thiophenemethanamine. No biological activity is reported for this compound.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new antiarthritic compounds with good antiinflammatory activity and minimal side effects that could be more effective in treating arthritis than presently available drugs.

In addition to antiinflammatory properties, some compounds of this invention have analgesic activity. This additional property is desirable in treatment of arthritis or related diseases; however, such compounds can be employed solely to alleviate pain.

SUMMARY OF THE INVENTION

This invention relates to novel antiinflammatory compounds of Formula I:

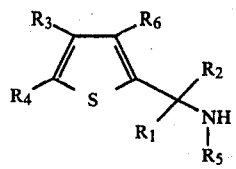

where
$R_1$ and $R_2$ independently = $CF_3$, $CF_2H$, $CFCl_2$, $CF_2Cl$, $CClFH$ or $CCl_2H$;
$R_3$ and $R_4$ independently = pyridyl or

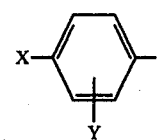

where
X=H, F, Cl, Br, $NO_2$, $C_1$-$C_2$ alkyl, $OR_7$, —$N(R_7)_2$ or $R_7S(O)_n$; where n=0, 1 or 2;
Y=H, F or Cl with the proviso that when Y is F or Cl, then X is F, Cl or H;
$R_5$=H or alkyl of 1-3 carbons;
$R_6$=H or alkyl of 1-3 carbons; and
$R_7$=alkyl of 1-2 carbons;

or a pharmaceutically suitable acid addition salt thereof.

Preferred compounds for utility considerations and/or ease of synthesis are where: $R_5$ and $R_6$=H and (a) at least one of $R_1$ and $R_2$=$CF_3$; or
(b) $R_3$ and $R_4$ independently =

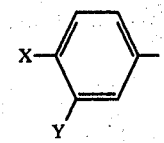

where
X=H, F, Br, Cl, $CH_3O$, $(CH_3)_2N$, $CH_3S(O)_n$; where n=0, 1 or 2; and Y=H.

More preferred compounds are where: $R_5$ and $R_6$=H and (a) $R_1$ and $R_2$=$CF_3$; or
(b) $R_3$ and $R_4$ independently =

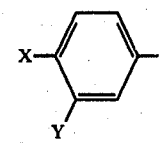

where
X=H, F, Cl, $CH_3S$ or $CH_3O$; and
Y=H.

Most preferred compounds are where:
$R_1$ and $R_2$=$CF_3$; and
$R_3$ and $R_4$ independently =

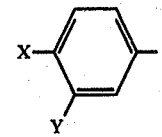

where
X=F or $CH_3S$;
Y=H; and
$R_5$ and $R_6$=H.

Specifically preferred compounds are:
4,5-bis(4-fluorophenyl)-α,α-bis(trifluoromethyl)-2-thiophenemethanamine; and
4-(4-fluorophenyl)-5-(4-methylthiophenyl)-α,α-bis(trifluoromethyl)-2-thiophenemethanamine.

Synthesis

The compounds of the invention may be prepared by the following reactions:

Method A

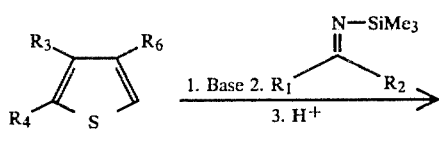

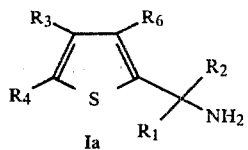

A 2,3-diarylthiophene II is reacted with a strong base such as n-butyl lithium or t-butyl lithium in an aprotic solvent such as tetrahydrofuran, diethyl ether or toluene optionally in the presence of a complexing agent such as tetramethylethylenediamine and then treated with a N-silylated halogenated ketone imine. The reaction can be carried out at a temperature from −78° to 110°.

The product from the previous step is then treated with aqueous acid at a temperature from 0° to 100° to give compound Ia.

Method B

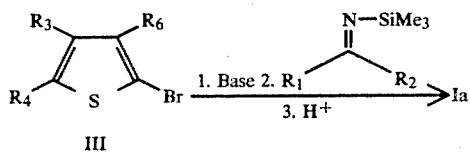

A 2-bromo-4,5-diarylthiophene III is treated with a strong base such as n-butyl lithium or t-butyl lithium in an aprotic solvent such as tetrahydrofuran, diethyl ether or toluene optionally in the presence of a complexing agent such as tetramethylethylenediamine at a temperature from −78° to 40°, preferably at −30° to 30° C. The resultant lithio thiophene is treated with a N-silyated halogenated ketone imine at a temperature from −78° to 110° and then treated with aqueous acid at a temperature from 0° to 100° to give compound Ia.

2-Bromo-4,5-diarylthiophenes are prepared by the reaction of a 2,3-diarylthiophene II with bromine (1 equivalent) in a solvent such as methylene chloride, acetic acid or their mixture at a temperature from −20° to 30°.

Method C

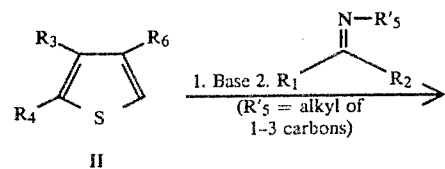

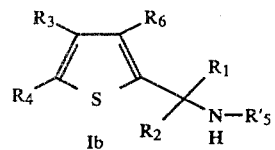

A 2,3-diarylthiophene II is reacted with a strong base such as n-butyl lithium or t-butyl lithium in an aprotic solvent such as tetrahydrofuran, diethyl ether or toluene optionally in the presence of a complexing agent such as tetramethylethylenediamine and then treated with a N-alkylated halogenated ketone imine to give compound Ib. The reaction can be carried out at a temperature from −78° to 100° C.

Method D

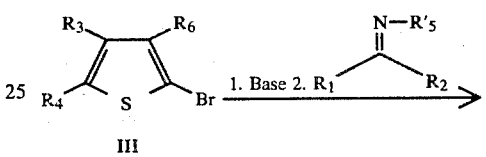

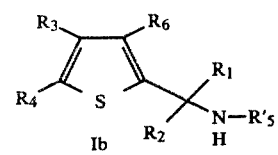

A 2-bromo-4,5-diarylthiophene is treated with a strong base such as n-butyl lithium or t-butyl lithium in an aprotic solvent such as tetrahydrofuran, diethyl ether or toluene optionally in the presence of a complexing agent such as tetramethylethylenediamine at a temperature from −78° to 40° C., preferably at −30° to 30° C. The resultant lithio thiophene is treated with a N-alkylated ketone imine at a temperature from −78° to 110° C. to give compound Ib.

Method E

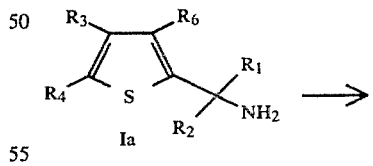

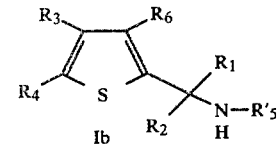

Compound Ia in an aprotic solvent such as tetrahydrofuran or dimethylformamide is treated with an alkylating agent such as methyl iodide or dimethyl sulfate in the presence of a base such a n-butyl lithium or sodium hydride to give compound Ib.

Method F

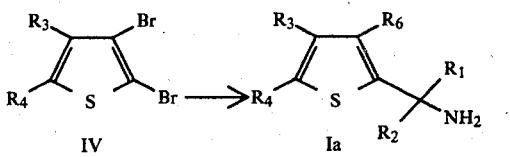

A dibromothiophene of structure IV in an aprotic solvent such as diethyl ether or tetrahydrofuran at a temperature from −78° to 35° C. is metallated with a reagent such as n-butyl lithium or magnesium and then treated with a N-silylated halogenated ketone imine. The resultant intermediate is further treated with a reagent such as n-butyl lithium or magnesium and then with an alkylating agent. Treatment with aqueous acid at a temperature from 0° to 100° then gives compound Ia.

2,3-Dibromo-4,5-diarylthiophenes IV are prepared by reaction of a 2,3-diarylthiophene with bromine (2 equivalents) in a solvent mixture such as methylene chloride and acetic acid at a temperature from 10° to 55°.

The compounds of the invention and their synthesis are illustrated further by the following examples. All temperatures are in degrees Centigrade.

ether, cooled to 0° and treated with 1.6 M n-butyl lithium (7 ml, 11 mmole). The reaction mixture was heated at reflux for 1.5 hours, cooled to 0° and treated dropwise with a solution of N-trimethylsilyl hexafluoroacetone imine (2.8 g, 12 mmole) in 5 ml diethyl ether. The reaction mixture was stirred for 4 hours at 0° and then quenched with water.

The aqueous phase was extracted with ethyl acetate and the combined organics washed with brine, dried and concentrated on the rotary evaporator.

The residue was dissolved in 100 ml ethanol, treated with 20 ml 1N HCl and heated at reflux for 20 minutes. The ethanol was removed in vacuo and the residue extracted with ethyl acetate. The organic extracts were washed with saturated aqueous $NaHCO_3$, 1N NaOH, and brine, dried and concentrated on the rotary evaporator. Chromatography on silica gel and recrystallization from hexanes gave the title compound (2.36 g), m.p. 87°–90°. Infrared and proton NMR spectra were consistent with the assigned structure. MS 461 (M+), 392 (M—$CF_3$).

Anal. Calcd. for $C_{21}H_{17}NO_2SF_6$: C, 54.66; H, 3.71; N, 3.04; Found: C, 54.5; H, 3.81; N, 3.02.

Using the appropriate N-silyated halogenated ketone imine, the following compounds can be prepared following the procedures outlined above and illustrated in the preceding example.

TABLE I

| Ex. No. | $R_1$ | $R_2$ | $R_3$ | $R_4$ | $R_6$ | m.p. (°C.) |
|---|---|---|---|---|---|---|
| 1 | $CF_3$ | $CF_3$ | 4-$CH_3O$—phenyl | 4-$CH_3O$—phenyl | H | 87–90° |
| 2 | $CF_3$ | $CF_3$ | 4-F—phenyl | 4-F—phenyl | H | 79–82° |
| 3 | $CF_3$ | $CF_3$ | 4-F—phenyl | 4-$CH_3S$—phenyl | H | 109–110° |
| 4 | $CF_3$ | $CF_3$ | 4-F—phenyl | 4-Cl—phenyl | H | 68–72° |
| 5 | $CF_3$ | $CF_3$ | phenyl | phenyl | H | 65–67° |
| 6 | $CF_3$ | $CF_2Cl$ | 4-F—phenyl | 4-F—phenyl | H | oil |
| 7 | $CF_3$ | $CF_2H$ | 4-F—phenyl | 4-F—phenyl | H | oil |
| 8 | $CF_3$ | $CF_3$ | 4-F—phenyl | 4-$(CH_3)_2N$—phenyl | H | |
| 9 | $CF_3$ | $CF_2H$ | 4-F—phenyl | 4-Br—phenyl | H | |
| 10 | $CF_2Cl$ | $CF_2Cl$ | 4-F—phenyl | 4-$CH_3SO$—phenyl | H | |
| 11 | $CF_3$ | $CF_3$ | 4-F—phenyl | 4-$CH_3SO_2$—phenyl | H | |
| 12 | $CF_3$ | $CF_3$ | 4-$NO_2$—phenyl | 4-F—phenyl | H | |
| 13 | $CF_3$ | $CF_3$ | 4-$CH_3$—phenyl | 4-$CH_3$—phenyl | H | 82–83° |
| 14 | $CF_3$ | $CF_3$ | phenyl | 3,4-$Cl_2$—phenyl | H | |
| 15 | $CF_2Cl$ | $CClFH$ | 4-F—phenyl | 4-F—phenyl | H | |
| 16 | $CF_3$ | $CCl_2H$ | 4-F—phenyl | 4-F—phenyl | H | |
| 17 | $CF_3$ | $CFCl_2$ | 4-F—phenyl | 4-F—phenyl | H | |
| 18 | $CF_3$ | $CF_3$ | 2-F—phenyl | 2-F—phenyl | H | oil |
| 19 | $CF_3$ | $CF_3$ | 4-F—phenyl | 2,4-$F_2$—phenyl | H | |
| 20 | $CF_3$ | $CF_3$ | 4-F—phenyl | 2,3-$F_2$—phenyl | H | |
| 21 | $CF_3$ | $CF_2Cl$ | 4-F—phenyl | 2-F,3-Cl—phenyl | H | |
| 22 | $CF_3$ | $CF_3$ | 4-F—phenyl | 2-F,4-Cl—phenyl | H | |
| 23 | $CF_3$ | $CF_3$ | 4-F—phenyl | 4-F—phenyl | $CH_3$ | |
| 24 | $CF_3$ | $CF_3$ | 4-F—phenyl | 4-F—phenyl | n-$C_3H_7$ | |
| 25 | $CF_3$ | $CF_3$ | 3-pyridyl | 4-F—phenyl | H | |
| 26 | $CF_3$ | $CF_3$ | 4-F—phenyl | 2-pyridyl | H | |
| 27 | $CF_3$ | $CF_3$ | 4-pyridyl | 4-F—phenyl | H | |

EXAMPLE 1

4,5-Bis(4-methoxyphenyl)-α,α-bis(trifluoromethyl)-2-thiophenemethanamine 2,3-Bis(4-methoxyphenyl)thiophene (2.96 g, 10 mmole) was dissolved in 75 ml toluene and the volume reduced by approximately two thirds by distillation. The cooled solution was diluted with 100 ml diethyl

EXAMPLE 28

1-[4,5-Bis(4-fluorophenyl)thiophen-2-yl]-2,2,2-trifluoro-1-trifluoromethyl-N-methylethanamine A solution of 2,3-bis(4-fluorophenyl)thiophene (5.4 g, 20 mmole) in 150 ml diethyl ether/30 ml toluene was cooled to 10° and treated with 1.6M n-butyl lithium (15 ml, 1.2 equiv.). The reaction mixture was heated at reflux for 1.5 hours, cooled to 0° and treated dropwise with a solution of N-methyl hexafluoroacetone imine (4.3 g, 1.2 equiv.) in 10 ml diethyl ether. The reaction mixture was stirred for 3 hours at 0° and then quenched with water.

The aqueous phase was extracted with ethyl acetate and the combined organics washed with brine, dried and concentrated on the rotary evaporator. Chromatography on silica gel using the Waters Prep LC/System 500 liquid chromatograph gave the title compound (1.9 g) as an oil. Infrared and proton NMR spectra were consistent with the assigned structure. MS 451 (M+), 382 (M—$CF_3$).

Using the appropriate N-alkylated halogenated ketone imine, the following compounds can be prepared following the procedures outlined above and illustrated in the preceding example.

TABLE II

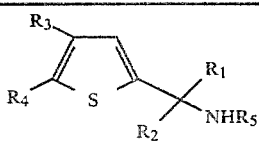

| Ex. No. | $R_1$ | $R_2$ | $R_3$ | $R_4$ | $R_5$ | m.p. (°C.) |
|---|---|---|---|---|---|---|
| 28 | $CF_3$ | $CF_3$ | 4-F—phenyl | 4-F—phenyl | $CH_3$ | oil |
| 29 | $CF_3$ | $CF_2H$ | 4-F—phenyl | 4-F—phenyl | $CH_3$ | |
| 30 | $CF_3$ | $CF_2Cl$ | 4-F—phenyl | 4-F—phenyl | $CH_3$ | |
| 31 | $CF_2Cl$ | $CF_2Cl$ | 4-F—phenyl | 4-F—phenyl | $C_2H_5$ | |
| 32 | $CF_3$ | $CF_3$ | phenyl | phenyl | $C_2H_5$ | |
| 33 | $CF_3$ | $CF_3$ | 4-F—phenyl | 4-F—phenyl | n-$C_3H_7$ | |
| 34 | $CF_3$ | $CF_3$ | 4-F—phenyl | 4-F—phenyl | i-$C_3H_7$ | |

Dosage Forms

The anti-arthritic agents and/or analgesic agents of this invention can be administered to treat arthritis and/or alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.2 to 50, and preferably 0.5 to 25 milligrams per kilogram per day given in divided doses 2 to 4 times a day or in sustained release form is effective to obtain desired results.

Dosage forms (compositions) suitable for internal administration contain from about 1.0 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl paraben, and chlorobutanol.

Suitable pharmaceutical carriers are described in Remington's Pharmaceutical Sciences, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 125 milligrams of lactose, 24 milligrams of talc, and 6 milligrams magnesium stearate.

Capsules

A mixture of active ingredient in soybean oil is prepared and injected by means of a positive displacement pump into gelatin to form soft gelatin capsules containing 100 milligrams of the active ingredient. The capsules are washed in petroleum ether and dried.

Tablets

A large number of tablets are prepared by conventional procedures so that the dosage unit is 100 milligrams of active ingredient, 0.2 milligrams of colloidal silicon dioxide, 4 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized by commonly used techniques.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Pharmaceutical Utility

A procedure for detecting and comparing the antiinflammatory activity of compounds in this series and standard drugs for which there is a good correlation with human efficacy is the adjuvant-induced arthritis test in rats.

The test procedure employed for determining antiinflammatory activity is described below.

Established Adjuvant-Induced Arthritis in Rats

Charles River Lewis male rats (130–150 grams) are injected subcutaneously in plantar area of the right hind paw with 0.1 ml of adjuvant (Difco heatkilled, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control Mean Paw Volume (ml)} - \text{Treatment Group Mean Paw Volume (ml)}}{\text{Arthritic Control Mean Paw Volume (ml)} - \text{Non-Arthritic Control Mean Paw Volume (ml)}} \times 100 =$$

% Decrease from Control Mean Paw Volume.

Dose-response regression lines of the % decrease are plotted on semi-log paper by visual fit and the ED50% decrease from control paw volume is determined by inspection.

Results

TABLE III

| Compound Example No. | Daily Oral Dose (mg/kg) | Percent Decrease From Control Paw Volume |
|---|---|---|
| 1 | 27 | 47[1] |
| 4 | 9 | 37[3] |
| 13 | 24 | 27[2] |
| 18 | 81 | 41[1] |

[1] $p < 0.001$ compared to control by Students "t" test.
[2] $p < 0.05$ compared to control by Students "t" test.
[3] $p < 0.1$ compared to control by Students "t" test.

TABLE IV

| Compound Example No. | ED50[4] (mg/kg) |
|---|---|
| 2 | 1.3 |
| 3 | 9 |
| 5 | 17 |
| 6 | 3.8 |
| 7 | 10.5 |
| 28 | 6.2 |
| Indomethacin | 0.25 |
| Phenylbutazone | 10 |
| Aspirin | 270 |

[4] ED$_{50}$ = effective dose (mg/kg) for 50% decrease from control paw volume.

What is claimed is:

1. A compound of the formula

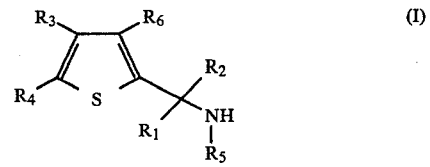

where
$R_1$ and $R_2$ independently = $CF_3$, $CF_2H$, $CFCl_2$, $CF_2Cl$, $CClFH$ or $CCl_2H$;
$R_3$ and $R_4$ independently = pyridyl or

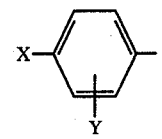

where
X = H, F, Cl, Br, NO$_2$, C$_1$–C$_2$ alkyl, OR$_7$, —N(R$_7$)$_2$ or R$_7$S(O)$_n$; where
n = 0, 1 or 2;
Y = H, F or Cl with the proviso that when Y is F or Cl, then X is F, Cl or H;
R$_5$ = H or alkyl of 1–3 carbons;
R$_6$ = H or alkyl of 1–3 carbons; and
R$_7$ = alkyl of 1–2 carbons;
or a pharmaceutically suitable acid addition salt thereof.

2. A compound of claim 1 where R$_6$ = H.

3. A compound of claim 2 where
R$_1$ and R$_2$ independently = CF$_3$, CF$_2$H, CFCl$_2$, CF$_2$Cl, CClFH or CCl$_2$H;
R$_3$ and R$_4$ independently = pyridyl or

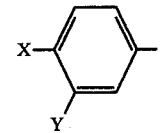

where
X = H, F, Cl, Br, NO$_2$, C$_1$–C$_2$ alkyl, OR$_7$, —N(R$_7$)$_2$ or R$_7$S(O)$_n$; where
n = 0, 1 or 2;
Y = H, F or Cl with the proviso that when Y is F or Cl, then X is F or Cl;
R$_5$ = H; and
R$_7$ = alkyl of 1–2 carbons.

4. A compound of claim 3 wherein at least one of R$_1$ and R$_2$ = CF$_3$.

5. A compound of claim 3 wherein

R₃ and R₄ independently =

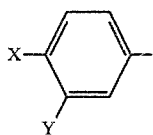

where
X=H, F, Br, Cl, CH₃O, (CH₃)₂N, CH₃S(O)$_n$; where n=0, 1 or 2; and
Y=H.

6. A compound of claim 3 wherein
at least one of R₁ and R₂=CF₃; and
R₃ and R₄ independently =

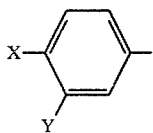

where
X=H, F, Br, Cl, CH₃O, (CH₃)₂N, CH₃S(O)$_n$; where n=0, 1 or 2; and
Y=H.

7. A compound of claim 3 wherein R₁ and R₂=CF₃.
8. A compound of claim 3 wherein
R₃ and R₄ independently =

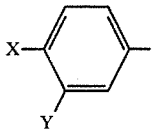

where
X=H, F, Cl, CH₃S or CH₃O; and
Y=H.

9. A compound of claim 3 wherein
R₁ and R₂=CF₃; and
R₃ and R₄ independently =

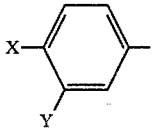

where
X=F or CH₃S; and
Y=H.

10. The compound of claim 2 which is 4,5-bis(4-fluorophenyl)-α,α-bis(trifluoromethyl)-2-thiophenemethanamine.

11. The compound of claim 2 which is 4-(4-fluorophenyl)-5-(4-methylthiophenyl)-α,α-bis(trifluoromethyl)-2-thiophenemethanamine.

12. A pharmaceutical composition consisting essentially of a suitable pharmaceutical carrier and an effective antiinflammatory amount of a compound of claim 1.

13. A pharmaceutical composition consisting essentially of a suitable pharmaceutical carrier and an effective antiinflammatory amount of a compound of claim 2.

14. A pharmaceutical composition consisting essentially of a suitable pharmaceutical carrier and an effective antiinflammatory amount of a compound of claim 3.

15. A pharmaceutical composition consisting essentially of a suitable pharmaceutical carrier and an effective antiinflammatory amount of a compound of claim 4.

16. A pharmaceutical composition consisting essentially of a suitable pharmaceutical carrier and an effective antiinflammatory amount of a compound of claim 5.

17. A pharmaceutical composition consisting essentially of a suitable pharmaceutical carrier and an effective antiinflammatory amount of a compound of claim 6.

18. A pharmaceutical composition consisting essentially of a suitable pharmaceutical carrier and an effective antiinflammatory amount of a compound of claim 7.

19. A pharmaceutical composition consisting essentially of a suitable pharmaceutical carrier and an effective antiinflammatory amount of a compound of claim 8.

20. A pharmaceutical composition consisting essentially of a suitable pharmaceutical carrier and an effective antiinflammatory amount of a compound of claim 9.

21. A pharmaceutical composition consisting essentially of a suitable pharmaceutical carrier and an effective antiinflammatory amount of the compound of claim 10.

22. A pharmaceutical composition consisting essentially of a suitable pharmaceutical carrier and an effective antiinflammatory amount of the compound of claim 11.

23. A method of treating inflammation in a mammal which comprises administering to the mammal an antiinflammatory amount of a compound of claim 1.

24. A method of treating inflammation in a mammal which comprises administering to the mammal an antiinflammatory amount of a compound of claim 2.

25. A method of treating inflammation in a mammal which comprises administering to the mammal an antiinflammatory amount of a compound of claim 3.

26. A method of treating inflammation in a mammal which comprises administering to the mammal an antiinflammatory amount of a compound of claim 4.

27. A method of treating inflammation in a mammal which comprises administering to the mammal an antiinflammatory amount of a compound of claim 5.

28. A method of treating inflammation in a mammal which comprises administering to the mammal an antiinflammatory amount of a compound of claim 6.

29. A method of treating inflammation in a mammal which comprises administering to the mammal an antiinflammatory amount of a compound of claim 7.

30. A method of treating inflammation in a mammal which comprises administering to the mammal an antiinflammatory amount of a compound of claim 8.

31. A method of treating inflammation in a mammal which comprises administering to the mammal an antiinflammatory amount of a compound of claim 9.

32. A method of treating inflammation in a mammal which comprises administering to the mammal an antiinflammatory amount of the compound of claim 10.

33. A method of treating inflammation in a mammal which comprises administering to the mammal an antiinflammatory amount of the compound of claim 11.

* * * * *